United States Patent [19]

Katsumata et al.

[11] Patent Number: 4,517,389

[45] Date of Patent: May 14, 1985

[54] PROCESS FOR METHYLATING THE ORTHO POSITION OF A PHENOL

[75] Inventors: Tsutomu Katsumata; Masahisa Yokota, both of Kanagawa, Japan

[73] Assignee: Asahi Kasei Kogyo Kabushiki Kaisha, Osaka, Japan

[21] Appl. No.: 521,205

[22] Filed: Aug. 8, 1983

[30] Foreign Application Priority Data

| Aug. 10, 1982 | [JP] | Japan | 57-137931 |
| Sep. 3, 1982 | [JP] | Japan | 57-152675 |
| Oct. 5, 1982 | [JP] | Japan | 57-173852 |
| Feb. 7, 1983 | [JP] | Japan | 58-18573 |

[51] Int. Cl.$^3$ .............................. C07C 37/16
[52] U.S. Cl. .................... 568/804; 568/780; 568/794
[58] Field of Search .................. 568/804, 794, 780

[56] References Cited

U.S. PATENT DOCUMENTS

| 2,075,507 | 11/1937 | Fremery et al. | 568/804 |
| 3,446,856 | 5/1969 | Hamilton | 568/804 |
| 3,855,318 | 12/1974 | Nakajima et al. | 568/804 |
| 3,953,529 | 4/1976 | Yonemitsu et al. | 568/804 |
| 3,972,836 | 8/1976 | Van Sorge | 252/471 |
| 3,974,229 | 8/1976 | Van Sorge | 568/804 |
| 4,024,195 | 5/1977 | Yonemitsu et al. | 568/804 |
| 4,059,544 | 11/1977 | Yamaguchi et al. | 252/471 |
| 4,227,023 | 10/1980 | Kawamata et al. | 568/804 |
| 4,301,308 | 11/1981 | Canavesi et al. | 568/804 |
| 4,329,517 | 5/1982 | Taniguchi et al. | 568/804 |
| 4,359,591 | 5/1982 | Fremery et al. | 568/804 |
| 4,361,709 | 11/1982 | Kawamata et al. | 568/804 |
| 4,400,557 | 8/1983 | Fremery | 568/804 |
| 4,429,171 | 6/1984 | Sakurai et al. | 568/804 |

FOREIGN PATENT DOCUMENTS

| 907064 | 8/1972 | Canada | 568/794 |
| 47-37942 | 9/1972 | Japan | 568/804 |
| 49331 | 5/1981 | Japan | 568/804 |
| 7512390 | 4/1976 | Netherlands | 568/804 |
| 717588 | 10/1954 | United Kingdom | 568/804 |
| 2089343 | 6/1982 | United Kingdom | 568/804 |

Primary Examiner—Werren B. Lone
Attorney, Agent, or Firm—Sprung Horn Kramer & Woods

[57] ABSTRACT

By flowing a gaseous stream containing methanol and a phenol through a fluidized bed of particles of a highly attrition resistant catalyst comprising 10 to 80% by weight of silica and 90 to 20% by weight of a metal oxide supported on the silica and have been calcined at 500° to 900° C., the ortho position of the phenol is methylated with high selectivity, whereby various useful ortho-methylated phenol derivatives can be advantageously obtained.

3 Claims, No Drawings

PROCESS FOR METHYLATING THE ORTHO POSITION OF A PHENOL

This invention relates to a process for methylating the ortho position of a phenol which is suitable for the production of ortho-methylated derivatives of phenol on a commercial scale. More particularly, the present invention is concerned with a process for methylating a phenol at the ortho position which comprises flowing a gaseous stream containing methanol and a phenol through a fluidized bed of particles of a catalyst calcined at 500° to 900° C. and comprising 10 to 80% by weight of silica and 90 to 20% by weight of a metal oxide supported on said silica.

Ortho-methylated derivatives of phenol are commercially useful because they are used as raw materials in the preparation of plastics, pharmaceuticals, agricultural chemicals and the like. For example, 2,6-xylenol is a precursor of valuable polymeric materials such as polyphenylene ethers; o-cresol is a precursor of pharmaceuticals, agricultural chemicals and the like; and 2,3,6-trimethyl phenol is a precursor of vitamin E and the like. Such ortho-methylated derivatives of phenol are generally produced by a fixed bed process which comprises flowing a gaseous stream containing methanol and a phenol having at least one hydrogen atom at the ortho position through a fixed bed of particles of a catalyst. As catalysts used in the preparation of the ortho-methylated derivatives of phenol by the fixed bed process, there are known various catalysts, e.g., an alumina catalyst (British Pat. No. 717,588), a magnesium oxide catalyst (U.S. Pat. No. 3,446,856), and a catalyst containing iron oxide and vanadium oxide (U.S. Pat. No. 3,855,318). Besides the above-mentioned catalysts, manganese oxide and chromium oxide are also known as catalysts which have a catalytic activity in the methylation of the ortho position of a phenol. However, the ortho-methylation of a phenol by the fixed bed process is accompanied by a problem with respect to control of the temperature in the fixed bed reactor. Close control of reaction variables is well known to be important in obtaining maximum yields of desired products. Of the several variables, temperature is one of the most important. Also in the ortho methylation of a phenol, close control of temperature is very important. The reason for this is that when methanol is reacted with a phenol in the vapor phase, the decomposition of methanol necessarily occurs in greater or lesser degree. Particularly, when temperature distribution in the reactor used is broad, the decomposition of methanol occurs in a great degree, causing the lowering of selectivity for the ortho-methylated phenol derivatives based on methanol. Therefore, in order to effect the methylation of the ortho position of a phenol in the vapor phase with a minimum degree of the decomposition of methanol, the temperature in the reactor should be uniformly maintained. In this respect, the fixed bed process is not suitable for the methylation of a phenol. As is well known, the fixed bed process is inherently defective in control of temperature. Further, the reaction of methanol with a phenol is highly exothermic. Therefore, when such a reaction is effected using a fixed bed reactor, localized heating tends to occur; particularly, with such a large fixed bed reactor as used on a commercial scale production, extreme difficulties are encountered in avoiding the localized heating. Due to the occurrence of such a localized heating, the decomposition of methanol occurs in a great degree, causing the lowering of selectivity for the ortho-methylated phenol dirivatives based on methanol, and further, the catalyst life, and the yield of and selectivity for the ortho-methylated phenol derivatives based on a phenol used as raw material are also decreased. Because of the above-mentioned drawbacks, the methylation of the ortho position of a phenol by the fixed bed process has not been regarded as an advantageous method from the commercial point of view.

On the other hand, a fluidized bed process which comprises flowing a gaseous stream containing reactants through a fluidized bed of particles of a catalyst has a great advantage of being capable of closely controlling the temperature over the fixed bed process. The close control of temperature which is possible in a fluidized bed is due to a combination of the following three factors: (1) turbulence within the fluidized mass; (2) high heat capacity of the bed relative to the gas within it; and (3) high heat-transfer rates which are possible because of the large amount of transfer surface per unit volume of the fluidized bed. Further advantages of the fluidized bed process will be described below. Most catalysts gradually lose their activity during the use because of poisoning or coating of the active surface with by-products and the like. Replacement or regeneration of the spent catalysts is therefore eventually required. In the case of the fixed bed process, as the activity decreases, operating conditions must be altered in order to maintain operating rate. Use of higher temperature is one expedient, but this may increase the cost of the product. Lowering the operating rate is another expedient, but this also results in increased cost through higher investment because the plant must be large enough to manufacture at an average rate sufficient to compensate for the low-rate period. In contrast, the fluidized bed process makes possible the maintenance of a definite level of catalyst activity because partially spent catalyst can be continuously withdrawn and fresh catalyst can be added. Further, in the case of the fluidized bed process, a complete regeneration of the catalyst can be attained by means of oxidation using air in a short period of time as compared with the regeneration of the catalyst of the fixed bed process. This is owing to the above-mentioned high heat transfer rates of the fluidized bed.

As mentioned above, the fluidized bed process has various advantages over the fixed bed process. However, the methylation of the ortho position of a phenol has not been carried out by the fluidized bed process on a commercial scale. The reason for this will be specifically explained below. In general, when a catalyst is used in a fluidized bed reactor, the particles of the catalyst come into collision with one another and with the inner wall of the reactor and are caused to be attrited. Therefore, the catalyst to be used in the fluidized bed process is required to have a sufficient attrition resistance. However, with respect to the methylation of the ortho position of a phenol by the fluidized bed process, there have, heretofore, been proposed no catalysts having a sufficient attrition resistance. This is attributable to a particular characteristic of the catalytic reaction of methanol with a phenol. Specifically, even in the catalytic reaction of methanol with a phenol by the fixed bed process, particles of a catalyst comprising a metal oxide such as an oxide of Fe, V, Mn, Mg, Cr or In tend to be fractured or powdered. The reason for this is believed to be as follows: (1) carbon is deposited on catalyst particles, followed by swelling, fracture and powdering of the catalyst particles; (2) catalysts, especially catalysts comprising metal oxides such as Fe, V and Mn undergo reduction to a great extent at the time of the reaction of methanol with a phenol; or (3) at the time of the regeneration of the catalyst by means of oxidation using air, the catalyst is chemically or thermally degraded. With respect to a catalyst for the fixed bed process, in order to avoid the fracture or powdering of the catalyst particles, there have been made various proposals. For example, Japanese Patent Application Publication Nos. 51-42092 (1976) and 51-10226 (1976) disclose a method in which cerium oxide, vanadium oxide or a combined iron and vanadium oxides is used as the catalyst and, further, water is added to the raw materials to be fed to the fixed bed reactor; U.S. Pat. Nos. 3,972,836 and 3,974,229 each disclose a catalyst having an improved catalyst life which comprises mangesium oxide mixed with and bonded by manganese oxide; and U.S. Pat. No. 4,059,544 discloses a composite type catalyst in which the surface of the particles of manganese oxide is covered with alumina. However, the above-mentioned method and catalysts disclosed in prior art cannot be satisfactorily applied to the methylation of the ortho position of a phenol by the fluidized bed process because such catalysts are still insufficient in attrition resistance. Meanwhile, U.S. Pat. No. 4,301,308 discloses a method of methylating the ortho position of a phenol by the fluidized bed process using alumina as the catalyst. However, this method is disadvantageous from the commercial point of view in that a large amount of anisole is unfavorably produced as a by-product, that the selectivity for the ortho-methylated phenol derivatives based on the phenol is poor, and that alumina is poor in attrition resistance.

The present inventors have made extensive and intensive studies with a view to developing a catalyst for the methylation of the ortho position of a phenol which has not only a high selectivity for the ortho-methylated phenol derivatives but also a high attrition resistance sufficient for the fluidized bed process. As a result, the present inventors have found that a catalyst calcined at 500° to 900° C. and comprising 10 to 80% by weight of silica and 90 to 20% by weight of a metal oxide having a catalytic activity in the methylation of the ortho position of a phenol supported on said silica not only exhibits a high attrition resistance in the fluidized bed process for the methylation of the ortho position of a phenol for a long period of time but also has a high selectivity for the ortho methylated phenol derivatives. The present invention has been made based on such a novel finding.

Accordingly, it is an object of the present invention to provide a process for effectively methylating the ortho position of a phenol which can be advantageously used for the production of ortho-methylated phenol derivatives on a commercial scale.

The foregoing and other objects, features and advantages of the present invention will be apparent to those skilled in the art from the following detailed description and appended claims.

In accordance with the present invention, there is provided a process for methylating a phenol at the ortho position which comprises flowing a gaseous stream containing methanol and a phenol having the general formula

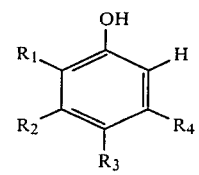

wherein $R_1$, $R_2$, $R_3$ and $R_4$ each independently represent a saturaated aliphatic hydrocarbon substituent selected from the group consisting of hydrogen, methyl, ethyl, isopropyl and tertiary butyl, through a fluidized bed of particles of a catalyst comprising 10 to 80% by weight of silica and 90 to 20% by weight of a metal oxide having a catalytic activity in the methylation of the ortho position of a phenol and supported on said silica, said catalyst having been calcined at 500° to 900° C.

Any phenol having at least one hydrogen atom at the ortho position may be selectively ortho-methylated by the process of the present invention. A phenol preferably ortho-methylated by the process of the present invention is represented by the general formula

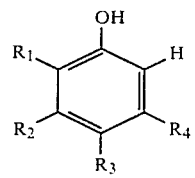

wherein $R_1$, $R_2$, $R_3$ and $R_4$ are as defined above. The above-mentioned phenols can be used alone or, if desired, in mixture.

As mentioned above, in the present process, a gaseous stream containing a phenol and methanol is flowed through a fluidized bed of particles of a catalyst comprising a metal oxide supported on silica to selectively methylate the ortho position of the phenol. In the catalyst to be used in the process of the present invention, silica should be employed as a support material. Silica is in itself inert as compared with other support materials and can serve as an excellent binder for an active ingredient and serve to impart to the resulting catalyst a high attrition resistance. If other material, e.g. alumina or silica-alumina is employed as a support material, the resulting catalyst has not only a poor attrition resistance but also causes the selectivity for ortho-methylated phenol derivatives based on a phenol to be lowered. The lowering of the selectivity for the ortho-methylated phenol derivatives based on a phenol is attributable to the formation of unfavorable by-products. For example, when phenol is ortho-methylated with methanol using as a catalyst comprising a metal oxide supported on alumina or silica-alumina, m-cresol, p-cresol and anisole are simultaneously produced in a large amount, in addition to 2,6-xylenol and o-cresol. As is well known, 2,6-xylenol is mainly used to prepare a polyphenylene ether (PPE) and is required to have an extremely high degree of purity. The presence of m-cresol and p-cresol even in a small amount in 2,6-xylenol to be used for the preparation of PPE causes a serious problem with respect to properties and yield of the resulting PPE. The difference in boiling point between 2,6-xylenol and m- and p-cresols is only 1° C. Therefore, the separation of 2,6-xylenol from m- and p-cresols is burdensome and cannot be attained by means of distillation. Therefore, it is very important in the methylation of the ortho position of a phenol that the reaction of a phenol with methanol be conducted while suppressing the formation of unfavorable by-products such as m- and p-cresols. In view of the above, alumina and silica-alumina are not suitable for use as a support material of the catalyst. In case diatomaceous earth, silicon carbide or zirconia is used as a support material for the catalyst, it can hardly exert a binding effect and, hence, the resulting catalyst is poor in attrition resistance. Therefore, such a catalyst cannot be satisfactorily used in the fluidized bed process. Further, diatomaceous earth, silicon carbide and zirconia cause the selectivity for the ortho-methylated phenol derivatives based on the phenol to be lowered.

The amount of silica to be used in the present invention should be in the range of 10 to 80% by weight, preferably 30 to 70% by weight based on the total weight of the catalyst. Where the amount of silica is less than 10% by weight, there cannot be obtained a sufficient attrition resistance. On the other hand, where the amount of silica exceeds 80% by weight, not only the activity of the catalyst and attrition resistance are lowered but also the selectivity for the resulting ortho-methylated phenol derivatives is lowered due to the increased formation of unfavorable by-products such as m- and p-cresols.

As mentioned above, the catalyst to be used in the process of the present invention contains 90 to 20% by weight, based on the total weight of the catalyst, a metal oxide as the active ingredient. Any metal oxide can be used as the active ingredient as far as the metal oxide has a catalytic activity in the methylation of the ortho position of a phenol. As examples of the metal component of the metal oxide which has an excellent catalytic activity in the methylation of the ortho position of a phenol, there may be mentioned at least one metal selected from the group consisting of iron, vanadium, manganese, magnesium, chromium and indium. Of the above-mentioned examples, more preferred metal components are iron, manganese and magnesium, and combinations of metals such as iron/vanadium, iron/chromium, iron/manganese, manganese/chriomium, manganese/magnesium and magnesium/chromium. When at least two metals are used as the metal component of the metal oxide, the atomic ratio of the metals is not critical as far as the metal oxide containing such metals as the metal component is supported on 10 to 80% by weight, based on the total weight of the catalyst, of silica. In the catalyst to be used in the process of the present invention, the metal oxide supported on silica may, in addition to the above-mentioned metal component (main metal component), further contains as an auxiliary metal component at least one metal selected from the group consisting of alkaline metals, alkaline earth metals and rare earth metals. The term "rare earth metals" as used herein includes the lanthanide elements, i.e., La, Ce, Pr, Nd, Pm, Sm, Eu, Gd, Tb, Dy, Ho, Er, Tm, Yb and Lu; Sc and Y. As the alkaline metals, at least one member selected from the group consisting of Li, Na, K, Rb and Cs are preferable and K and Rb are more preferable. As the alkaline earth metals, at least one member selected from the group consisting of Ca, Sr and Ba are preferable. As the rare earth metals, at least one member selected from the group consisting of La, Ce, Pr, Nd and Sm are preferable. The presence of the above-mentioned at least one metal as the auxiliary metal component in the metal oxide contributes to the improvement of catalyst life and selectivity for the ortho-methylated phenol derivatives. The amount of the auxiliary metal component in the metal oxide varies depending on metals used as the auxiliary metal component. However, in general, alkaline metals, alkaline earth metals and rare earth metals are respectively used in atomic ratios of 0.0001 to 0.1, 0.0001 to 0.5, and 0.0001 to 0.5 relative to the above-mentioned main metal component of the metal oxide. In case the auxiliary metal component is contained in the metal oxide in too large an amount, the activity of the catalyst and/or the selectivity for the ortho-methylated phenol derivatives are lowered.

As mentioned above, the catalyst to be used in the process of the present invention should have been calcined at 500° to 900° C. When the calcination temperature is less than 500° C., not only the catalytic activity is lowered but also the selectivity for unfavorable by-products such as m- and p-cresols is remarkably increased. When the calcination temperature is more than 900° C., the crystallinity of silica used as the support material is increased, causing the lowering in attrition resistance of the catalyst. A preferable calcination temperature of the catalyst is such as will keep the silica supporting thereon the metal oxide to be in substantially the amorphous state and, hence, varies depending on the metal component of the metal oxide. For example, where the metal component is composed mainly of iron or chromium, a more preferred calcination temperature is 550° to 750° C.; where, the metal component is composed mainly of vanadium or indium, a more preferred calcination temperature is 550° to 850° C.; where the metal component is composed mainly of manganese, a more preferred calcination temperature is 600° to 900° C.; and where the metal component is composed mainly of magnesium, a more preferred calcination temperature is 500° to 700° C.

In the present invention, it is preferred that the catalyst to be used in the process of the present invention have an average particle diameter of 30 to 120μ, more preferably 40 to 100μ, and have a particle size distribution such that the catalyst comprises (A) catalyst particles having particle diameters of 0.2 to 0.7 time the average particle diameter, (B) catalyst particles having particle diameters of 1.5 to 2.0 times the average particle diameter and (C) catalyst particles having particle diameters of more than 2.0 times the average particle diameter, the proportions of (A), (B) and (C) in the catalyst being 5 to 50%, 5 to 30% and 0 to 10% by weight, respectively, more preferably 10 to 40%, 10 to 20% and 0 to 5% by weight, respectively. The particle size distribution may be determined by the well known microscopic method. The term "average particle diameter" as used herein means such a particle diameter value that the total weight of catalyst particles having particle diameters larger than the value is equal to the total weight of catalyst particles having particle diameters smaller than the value. For example, an average particle diameter of 60μ means that the total weight of catalyst particles having particle diameters larger than 60μ is equal to the total weight of catalyst particles having particle diameters smaller than 60μ.

As is well known, in the fluidized bed process, the gas fed to the fluidized bed reactor rises through the fluidized bed in the form of bubbles. The bubbles repeat coalescence and break while rising through the bed. When the bubbles grow into too large bubbles, the gas-solids contact becomes poor. In an extreme case, the gas containing a phenol and methanol fed to the fluidized bed reactor rises through the fluidized bed without the contact of the gas with the catalyst particles. The above-mentioned poor gas-solids contact is caused by the insufficient fluidization of the catalyst particles. When this happens, not only the conversion of the phenol and selectivity for the ortho-methylated phenol derivatives are drastically lowered but also the temperature distribution in the fluidized bed becomes broad, causing the localized heating. Therefore, in such a case, the advantage of the fluidized bed process over the fixed bed process is spoiled. When the catalyst particles have the above-mentioned average particle diameter and particle size distribution, such catalyst particles are well fluidized by a gaseous stream fed to the fluidized bed reactor and an very excellent gas-solids contact can be attained, which enables the reaction temperature to be closely controlled and the selectivity for the ortho-methylated phenol derivatives to be increased. On the other hand, where the average particle diameter and the particle size distribution of the catalyst particles do not fall within the above-mentioned range, the contact of the gas with the catalyst particles becomes poor, causing the lowering of the conversion of a phenol and the selectivity for the ortho-methylated phenol derivatives based on the phenol; and there occurs a localized heating which causes not only the selectivity for the ortho-methylated phenol derivatives based on methanol to be lowered but also the catalyst life to be shortened.

In the process of the present invention, in order to well fluidize the catalyst particles, it is preferred that a gaseous stream containing methanol and a phenol be fed to the fluidized bed reactor at a linear velocity of 0.5 to 100 cm/sec, more preferably 2 to 80 cm/sec.

The catalyst to be used in the process of the present invention may be prepared by a method comprising (1) preparing a slurry or solution of raw materials, (2) spray-drying the resulting slurry or solution and (3) heat-treating the resulting spray-dried product for calcination thereof. As the source of silica used as a support material, there may be mentioned a silica sol, silica hydrogel, sodium silicate, alkylsiloxanes, silicon tetrachloride, etc. Of the above-mentioned sources, a silica sol is preferably employed. As the source of vanadium, its ammonium salt, chloride, oxy chloride and the like are generally employed, and an ammonium salt of vanadium is preferably employed. As the sources of iron, manganese, magnesium, chromium, indium and rare earth metals, there may be generally employed their nitrates, chlorides, sulfates, salts of organic acids and the like, and their nitrates are preferably employed. As the sources of alkaline metals and alkaline earth metals, their carbonates, nitrates, salts of organic acids and the like are generally used, and their nitrates are preferably employed.

In the step(1), as mentioned above, a solution or a slurry of raw materials is prepared. Specifically, a predetermined amount of a metal salt is dissolved in water. To the resulting solution is added a silica source to prepare a slurry having a good uniformity or a solution of raw materials.

In the step(2), the slurry or solution thus obtained is spray-dried using an ordinary spray-drying apparatus to obtain dried spherical particles. The spraying of the slurry or solution may be conducted by any type of methods usually employed e.g., a centrifugal type, a two-fluid nozzle type or a high pressure nozzle type spraying method, but the centrifugal type spraying method is particularly preferred. In the centrifugal type spraying method, the diameters of the product catalyst particles can be easily adjusted by varying the shape of the disc or by regulating the rotation speed of the disc and the rate of supply of the slurry so that there are obtained catalyst particles having an average particle diameter and particle size distribution suitable for use in the fluidized bed process.

In the step(3), the spray-dried product obtained in the step(2) is subjected to heat-treatment for calcination using an ordinarily employed kiln such as a tunnel type or a rotary type kiln. The calcination time is not critical but is generally one to several ten hours. As mentioned before, in the process of the present invention, the calcination temperature of the catalyst should be in the range of 500° to 900° C. That is, in preparing the catalyst to be used in the process of the present invention, the calcination temperature 500° to 900° C. is one of the most important. The calcination of the catalyst at 500° to 900° C. imparts to the catalyst a high attrition resistance sufficient for the fluidized bed process and an excellent catalytic activity for the methylation of the ortho position of a phenol.

In the process of the present invention, the molar ratio of a phenol relative to methanol varies depending on catalysts to be used but is generally 1:1 to 1:20, preferably 1:3 to 1:10. Further, it is possible to dilute the gaseous stream containing a phenol and methanol with steam or an inert gas such as $N_2$ or $CO_2$ according to need. When steam is used, the selectivity for the ortho-methylated phenol derivatives based on methanol is improved, while the inert gas is optionally used to control the flow rate of the gaseous stream to be fed to the fluidized bed reactor. However, the use of the inert gas or steam in too large an amount causes the productivity for the ortho-methylated phenol derivatives to be lowered.

The reaction temperature is generally 250° to 600° C. The preferred reaction temperature varies depending on the metal component of the metal oxide supported on silica. For example, where the metal component is composed mainly of iron or chromium, a preferred reaction temperature is 300° to 450° C.; where the metal component is composed mainly of vanadium or indium, a preferred reaction temperature is 250° to 400° C.; where the metal component is composed mainly of manganese, a preferred reaction temperature is 350° to 450° C.; and where the metal component is composed mainly of magnesium, a preferred reaction temperature is 400° to 550° C.

The reaction pressure is usually atmospheric. It is also possible to operate at a pressure higher or lower than atmospheric. When the reaction is carried out under reduced pressure, a low-cost heat source such as a high-pressure steam can be used. On the other hand, when the reaction is carried out under a super-atmospheric pressure, the productivity of ortho-methylated phenol derivatives per volume of the catalyst is increased.

The advantages of the process of the present invention will be summarized below.

(1) The specific catalyst calcined at 500° to 900° C. and comprising 10 to 80% by weight of silica and 90 to 20% by weight of a metal oxide supported thereon can maintain a high activity and selectivity stably for a long period of time without undergoing attrition, so that the desired ortho-methylated phenol derivatives can be produced in high yields.

(2) Since the methylation of the ortho position of a phenol is carried out by the fluidized bed process, close control of temperature can be attained even in such a large reactor as used for the production of ortho-methylated derivatives on a commercial scale. Therefore, the decomposition of methanol is minimized, and hence, a high selectivity for the ortho-methylated derivatives based on methanol can be attained.

(3) Because of the fluidized bed process, a complete regeneration of the catalyst can be attained by means of oxidation using air in a short period of time as compared with the fixed bed process.

(4) Partially spent catalyst can be continuously withdrawn and fresh catalyst can be added. Therefore, it is possible to carry out a continuous operation for a long period of time.

The present invention will now be illustrated in more detail by the following Examples that should not be construed as limiting the scope of the invention.

In Examples, the products of the methylation of the ortho position of a phenol were analyzed by gas chromatography.

Conversion of a phenol, selectivities for ortho-methylated phenol derivatives, and selectivity for by-products are those obtained by the following formulae:

Conversion of a phenol (%) = (1)

$$\frac{\text{mole number of consumed phenol}}{\text{mole number of fed phenol}} \times 100$$

Selectivity for an ortho-methylated phenol (2)
derivative based on phenol (%) =

$$\frac{\text{mole number of produced desired ortho-methylated derivative}}{\text{mole number of consumed phenol}} \times 100$$

Selectivity for an ortho-methylated phenol (3)
derivative based on methanol (%) =

$$\frac{\text{mole number of produced desired ortho-methylated derivative}}{\text{mole number of consumed methanol}} \times 100$$

Selectivity for m- and p-cresols as by-products (4)
(total value of selectivity for m-cresol and selectivity for p-cresol) (%) =

$$\frac{\text{(mole number of produced m-cresol)} + \text{(mole number of produced p-cresol)}}{\text{mole number of consumed phenol}} \times 100$$

The attrition resistances of catalysts were measured according to substantially the same test method for a FCC catalyst (catalyst for fluid catalytic cracking process).

About 50 g of a catalyst was weighed accurately and placed in a vertical tube having an internal diameter of 1.5 inches and a height of 30 inches and provided at the bottom with a perforated disc having three orifices whose diameters were each 1/64 inch. Air started to be introduced through the orifices of the perforated disc into the tube at a rate of 15 cubic feet/hour, whereby the catalyst was vigorously fluidized. The attrition degree of the catalyst was evaluated in terms of percentage of the weight of the fine catalyst particles produced by attrition and blown off from the top of the vertical tube during the period of from 5 hours to 20 hours, relative to the initial weight of the catalyst charged.

EXAMPLE 1

To a solution of 585 g of ammonium metavanadate($NH_4VO_3$) in 12,400 g of pure water heated at 90° C. were added, while stirring the solution, 2,020 g of ferric nitrate [$Fe(NO_3)_3 \cdot 9H_2O$] and 2,850 g of SNOWTEX-N (trademark of a silica sol manufactured and sold by Nissan Kagaku Kabushiki Kaisha, Japan) containing 30% by weight of $SiO_2$, whereby the raw material slurry was obtained. The thus obtained slurry was dried by means of a parallel flow type spray drier [hot-air temperature: 110° C. (at the outlet of the drier)]. In this step, the atomization of the slurry was done by means of a centrifugal type spraying apparatus equipped with a dish type rotor and disposed in the center of the upper part of the spray drier. The dried powder thus obtained was transferred to a tunnel type calcining kiln and precalcined at 350° C. for 2 hours, followed by calcination at 750° C. for 3 hours. Thus, a spherical catalyst comprising a metal oxide containing as the metal component vanadium and iron and supported on silica was obtained. The surface area of the obtained catalyst was 20.5 m$^2$/g as determined according to the BET method using nitrogen gas. The average particle diameter and particle size distribution of the catalyst particles were determined by the microscopic method.

Particle size range: 20 to 200$\mu$
Average particle diameter: 60$\mu$
Particle size distribution:
   0.2 to 0.7 time the average particle diameter; 35% by weight;
   1.5 to 2.0 times the average particle diameter; 16% by weight;
   More than 2.0 times the average particle diameter; 1.3% by weight.

300 g of the above-prepared catalyst was put into a 1.5 inch-diameter fluidized bed reactor. A mixture of phenol, methanol and water in a molar ratio of 1:5:3 was fed to an evaporator. The resulting gas was passed through the reactor at a linear velocity of 4.6 cm/sec to react phenol with methanol while maintaining the reaction temperature at 320° to 330° C. and the reaction pressure at zero (atmospheric pressure). The reaction product vapors were led to a condenser and receiver. A continuous operation for the methylation of phenol with methanol was carried out and the products were analyzed at the respective ends of the operation periods as indicated in Table 1. The results are shown in Table 1.

The catalyst was applied to the attrition resistance test before use in the reaction and after use in the reaction, and the obtained results are shown in Table 1.

EXAMPLES 2 TO 6 AND COMPARATIVE EXAMPLES 1 TO 5

Substantially the same procedures as in Example 1 were repeated to prepare catalysts as indicated in Table 1 except that the amount of silica and the calcination temperature as indicated in Table 1 were used.

The average particle diameter and particle size distribution of each catalyst were determined in the same manner as in Example 1, and the results are shown in Table 1. It was found by x-diffractometry that with the catalyst calcined at 1000° C. (Comparative Example 5), silica used as the support material was crystallized.

A continuous operation for the methylation of phenol with methanol was carried out in substantially the same manner as in Example 1 except that the above-prepared catalysts were used and that reaction conditions were varied as indicated in Table 1. The reaction products were analyzed in the same manner as in Example 1 and the results are shown in Table 1.

The above-prepared catalysts were applied to the attrition resistance tests before use in the reaction and after use in the reaction. The results are shown in Table 1.

EXAMPLES 7 TO 10

Substantially the same procedures as in Example 1 were repeated to prepare catalysts as indicated in Table 1, in which the metal oxide ingredient containing as the metal component V and F further contained an oxide of Mg, K, Ce or La. Mg(NO$_3$)$_2$.6H$_2$O, KNO$_3$, Ce(NO$_3$)$_3$.6H$_2$O and La(NO$_3$)$_3$.6H$_2$O were used as the sources of Mg, K, Ce and La, respectively.

The average particle diameter and particle size distribution of each catalyst were determined in the same manner as in Example 1, and the results are shown in Table 1.

A continuous operation for the methylation of phenol with methanol was carried out in substantially the same manner as in Example 1 except that the above-prepared catalysts were used and that reaction conditions were varied as indicated in Table 1. The reaction products were analyzed in the same manner as in Example 1 and the results are shown in Table 1.

The above-prepared catalysts were applied to the attrition resistance tests before use in the reaction and after use in the reaction. The results are shown in Table 1.

TABLE 1

| | Catalyst | | | | Particle diameter distribution | | | |
|---|---|---|---|---|---|---|---|---|
| Example No. | Metal Oxide Metal component and atomic ratio | Silica (% by weight) | Calcination temp. (°C.) | Average particle diameter (μ) | 0.2 to 0.7 time the average particle diameter (%) | 1.5 to 2.0 times the average particle diameter (%) | More than 2.0 times the average particle diameter (%) | Molar ratio of raw materials (Phenol: methanol: water) |
| Example 1 | V:Fe = 1:1 | 50 | 750 | 60 | 35 | 16 | 1.3 | 1:5:3 |
| Example 2 | " | 40 | 700 | 60 | 35 | 15 | 1.1 | 1:5:0 |
| Example 3 | " | 60 | 700 | 57 | 31 | 15 | 2.2 | " |
| Example 4 | " | 70 | 700 | 60 | 33 | 17 | 2.0 | 1:6:3 |
| Example 5 | " | 50 | 650 | 60 | 35 | 16 | 1.3 | 1:5:3 |
| Example 6 | " | 50 | 800 | 60 | 35 | 16 | 1.3 | " |
| Example 7 | V:Fe:Mg = 1:1:0.1 | 50 | 750 | 50 | 32 | 14 | 1.1 | " |
| Example 8 | V:Fe:K = 1:1:0.025 | 50 | 680 | 48 | 34 | 17 | 1.0 | " |
| Example 9 | V:Fe:K:Ce = 1:1:0.015:0.1 | 50 | 680 | 50 | 34 | 17 | 1.2 | " |
| Example 10 | V:Fe:K:La = 1:10:0.015:0.1 | 50 | 680 | 49 | 35 | 15 | 1.2 | " |
| Comparative Example 1 | V:Fe = 1:1 | 0 | 750 | 55 | 30 | 15 | 1.3 | " |
| Comparative Example 2 | " | 5 | 750 | 55 | 34 | 18 | 1.5 | " |
| Comparative Example 3 | " | 50 | 450 | 60 | 35 | 16 | 1.3 | " |
| Comparative Example 4 | " | 95 | 700 | 50 | 32 | 15 | 1.7 | " |
| Comparative Example 5 | " | 50 | 1000 | 60 | 29 | 18 | 1.8 | " |

| | Reaction Conditions | | | Results | | | | | Attrition degree of catalyst (%) | |
|---|---|---|---|---|---|---|---|---|---|---|
| Example No. | Linear velocity of gaseous stream (cm/sec) | Reaction time (hr) | Reaction Temp. (°C.) | Conversion of phenol (%) | Selectivity for ortho-methylated product based on phenol (%) A 2,6-xylenol | B o-cresol | A + B | Selectivity for m- and p-cresols based on phenol (%) | Before use in reaction | After use in reaction |
| Example 1 | 4.6 | 24 | 320 | 83.0 | 44.1 | 53.3 | 97.4 | 0.02 | 0.80 | 1.35 |
| | 120 | 322 | | 82.8 | 43.5 | 54.2 | 97.7 | 0.02 | | |
| | 240 | 325 | | 82.7 | 43.0 | 54.9 | 97.9 | 0.02 | | |
| Example 2 | 6.9 | 24 | 320 | 82.4 | 54.6 | 42.6 | 97.2 | 0.02 | 1.60 | 1.9 |
| Example 3 | 4.7 | 24 | " | 83.0 | 54.4 | 43.1 | 97.5 | 0.02 | 0.55 | 0.8 |
| Example 4 | 5.0 | 24 | 330 | 89.7 | 70.5 | 27.0 | 97.5 | 0.02 | 0.9 | 1.0 |
| Example 5 | 5.0 | " | 320 | 77.4 | 51.8 | 45.2 | 97.0 | 0.03 | 1.5 | 1.8 |
| Example 6 | 4.6 | " | 320 | 82.5 | 49.3 | 48.2 | 97.5 | 0.02 | 0.7 | 1.2 |
| | | 120 | 323 | 82.0 | 48.6 | 49.3 | 97.9 | 0.02 | | |
| Example 7 | 4.8 | 24 | 320 | 81.7 | 47.1 | 49.7 | 96.8 | 0.01 | 1.1 | 1.7 |
| Example 8 | 4.6 | 24 | 330 | 86.3 | 61.1 | 37.4 | 98.5 | 0.00 | 1.3 | 1.5 |
| Example 9 | 4.6 | 24 | 320 | 83.1 | 54.9 | 43.5 | 98.4 | 0.00 | 1.2 | 1.6 |
| Example 10 | 4.6 | 24 | " | 84.3 | 58.9 | 39.6 | 98.5 | 0.00 | 1.3 | 1.6 |
| Comparative Example 1 | 8.5 | 24 | 320 | 88.5 | 55.3 | 41.4 | 96.7 | 0.03 | 4.6 | 9.3 |
| | | 72 | | 79.6 | 44.8 | 51.8 | 96.6 | 0.03 | | |
| Comparative Example 2 | 8.8 | 24 | " | 87.0 | 54.0 | 42.5 | 96.5 | 0.02 | 4.0 | 9.0 |
| | | 48 | | 82.6 | 50.1 | 46.5 | 96.6 | 0.02 | | |
| Comparative Example 3 | 4.6 | 24 | " | 50.3 | 18.5 | 76.5 | 95.0 | 0.81 | 1.8 | 4.0 |
| | | 120 | | 34.0 | 12.0 | 82.5 | 94.5 | 0.95 | | |
| Comparative Example 4 | 2.7 | 24 | 330 | 17.7 | 7.5 | 86.1 | 93.6 | 1.32 | 3.4 | 6.5 |
| Comparative Example 5 | 4.6 | 24 | 320 | 62.7 | 20.9 | 74.2 | 95.1 | 0.15 | 10.0 | 18.7 |

EXAMPLE 11 TO 14 AND COMPARATIVE EXAMPLES 6 AND 7

Catalysts comprising silica and a metal oxide containing metal components as indicated in Table 2 were prepared in substantially the same manner as in Example 1. $Fe(NO_3)_3.9H_2O$, $Cr(NO_3)_3.9H_2O$, $Mn(NO_3)_2.6H_2O$, and $Mg(NO_3)_2.6H_2O$ were used as the sources of Fe, Cr, Mn and Mg, respectively.

The average particle diameter and particle size distribution of each catalyst were determined in the same manner as in Example 1, and the results are shown in Table 2.

A continuous operation for the methylation of phenol with methanol was carried out in substantially the same manner as in Example 1 except that the above-prepared catalysts were used and that reaction conditions were varied as indicated in Table 2. The reaction products were analyzed in the same manner as in Example 1 and the results are shown in Table 2.

The above-prepared catalysts were applied to the attrition resistance tests before use in the reaction and after use in the reaction. The results are shown in Table 2.

COMPARATIVE EXAMPLE 9

105 g of a diatomaceous earth was impregnated with 183.9 g of manganese nitrate, followed by calcination at 700° C. for 3 hours. The resulting catalyst was applied to the attrition resistance test. The result is shown in Table 3.

TABLE 3

| Example | Catalyst Metal Oxide Metal Component | Support material Kind | Support material Amount (% by weight) | Attrition degree (%) |
|---|---|---|---|---|
| Comparative Example 8 | Mn | Alumina | 70 | 8.0 |
| Comparative Example 9 | Mn | diatomaceous | 70 | 6.5 |

EXAMPLE 15

Using the same catalyst and reactor as in Example 1, a continuous operation for the methylation of a phenol with methanol was carried out in substantially the same manner as in Example 1 except that o-cresol was used instead of phenol. The reaction temperature, linear velocity and a molar ratio of o-cresol, methanol and water were 320° C., 4.6 cm/sec and 1:3:3, respectively. The conversion of o-cresol and the selectivity for 2,6-xylenol based on o-cresol were determined at the end of a 24-hour operation period. The conversion of o-cresol was 99.5% and the selectivity for 2,6-xylenol based on o-cresol was 98.5%.

TABLE 2

| Example No. | Metal Oxide Metal component and atomic ratio | Silica (% by weight) | Calcination temp. (°C.) | Average particle diameter (μ) | Particle diameter distribution 0.2 to 0.7 time the average particle diameter (%) | Particle diameter distribution 1.5 to 2.0 times the average particle diameter (%) | Particle diameter distribution More than 2.0 times the average particle diameter (%) | Molar ratio of raw materials (Phenol: methanol: water) |
|---|---|---|---|---|---|---|---|---|
| Example 11 | Fe | 50 | 700 | 45 | 30 | 17 | 2.1 | 1:6:3 |
| Example 12 | Fe:Cr = 1:0.1 | 50 | 500 | 56 | 35 | 14 | 1.0 | 1:8:0 |
| Example 13 | Mn | 30 | 750 | 53 | 33 | 16 | 1.7 | 1:8:0 |
| Example 14 | Mg | 50 | 600 | 60 | 25 | 20 | 2.0 | 1:5:3 |
| Comparative Example 6 | Mg | 50 | 350 | 57 | 29 | 18 | 1.8 | 1:5:3 |
| Comparative Example 7 | Mg | 50 | 1000 | 57 | 29 | 18 | 1.8 | 1:5:3 |

| Example No. | Reaction Conditions Reaction Temp. (°C.) | Reaction Conditions Linear velocity of gaseous stream (cm/sec) | Reaction Conditions Reaction time (hr) | Results Conversion of phenol (%) | Results Selectivity for ortho-methylated product based on phenol (%) A 2,6-xylenol | Results Selectivity for ortho-methylated product based on phenol (%) B o-cresol | Results A + B | Attrition degree of catalyst (%) Before use in reaction | Attrition degree of catalyst (%) After use in reaction |
|---|---|---|---|---|---|---|---|---|---|
| Example 11 | 330 | 4.6 | 24 | 91.8 | 56.1 | 40.0 | 96.1 | 1.7 | 1.8 |
| Example 12 | 350 | 4.6 | 24 | 90.7 | 54.8 | 42.2 | 97.1 | 1.5 | 1.8 |
| Example 13 | 400 | 4.6 | 24 | 90.5 | 52.3 | 45.0 | 97.3 | 1.7 | 2.0 |
| Example 14 | 550 | 4.6 | 24 | 95.0 | 66.0 | 31.0 | 97.0 | 1.3 | 1.7 |
| Comparative Example 6 | 550 | 4.6 | 24 | 70.6 | 35.0 | 60.2 | 95.2 | 4.1 | 5.9 |
| Comparative Example 7 | 550 | 4.6 | 24 | 67.1 | 23.1 | 71.7 | 94.8 | 7.0 | 9.1 |

COMPARATIVE EXAMPLE 8

183.9 g of manganese nitrate [$Mn(NO_3)_2.6H_2O$] was added in 1,050 g of an alumina sol containing 10% by weight of $Al_2O_3$. In substantially the same manner as in Example 1, the resulting solution was atomized and dried, followed by calcination at 700° C. for 3 hours. The resulting catalyst was applied to the attrition resistance test. The result is shown in Table 3.

EXAMPLE 16

Using the same catalyst as in Example 8 and the same reactor as in Example 1, a continuous operation for the methylation of m-cresol with methanol was carried out. The reaction temperature, linear velocity and the molar ratio of m-cresol, methanol and water were 320° C., 6 cm/sec and 1:5:3, respectively. The conversion of m-cresol and selectivity for 2,3,6-trimethyl phenol based on m-cresol were determined at the end of a 24-hour operation period. The conversion of m-cresol and selectivity for 2,3,6-trimethyl phenol based on m-cresol were 99.6% and 94.0%, respectively.

EXAMPLE 17

2531.4 g of ferric nitrate [Fe(NO$_3$)$_3$.9H$_2$O], 24.82 g of chromic nitrate [Cr(NO$_3$)$_3$.9H$_2$O] and 0.317 g of potassium nitrate (KNO$_3$) were dissolved in 2,500 g of pure water. To the resulting solution as added 500 g of SNOWTEX-N (trademark of a silica sol manufactured and sold by Nissan Kagaku Kabushiki Kaisha, Japan) containing 30% by weight of SiO$_2$, whereby the raw material slurry was obtained. The thus obtained slurry was dried in the same manner as in Example 1. The obtained dry powder was ball-milled, followed by sifting through a 325-mesh sieve. 500 g of the obtained finly divided powder was added to a mixture of 1,000 g of pure water and 897.4 g of a silica sol containing 30% by weight of SiO$_2$. While vigorously stirring, the resulting slurry was spray-dried in the same manner as in Example 1. The dried powder thus obtained was calcined at 680° C. for 3 hours, whereby there was obtained a catalyst comprising a metal oxide containing as the metal component Fe, Cr and K in an atomic ratio of 1:0.01:0.0005 and supported on 50% by weight, based on the catalyst, of silica. It was confirmed by means of an electron microscope that the catalyst particles had a spherical shape suitable for use in the fluidized bed process. The surface area of the catalyst was 31.1 m$^2$/g as determined according to the BET method using nitrogen gas. The average particle diameter and particle size distribution of the catalyst particles were determined by the microscopic method.
Particle size range: 20 to 200μ
Average particle diameter: 75μ
Particle size distribution:
  0.2 to 0.7 time the average particle diameter; 20% by weight
  1.5 to 2.0 times the average particle diameter; 20% by weight;
  More than 2.0 times the average particle diameter; 3% by weight.

A continuous operation for the methylation of phenol with methanol was carried out in substantially the same manner as in Example 1, except that the above-prepared catalyst was used and that the reaction temperature was controlled at 330° C. The conversion of phenol, selectivities for 2,6-xylenol and o-cresol were determined at the end of a 24-hour operation period. The results were as follows.
Conversion of phenol: 84.4%
Selectivity for 2,6-xylenol based on phenol (A): 50.1%
Selectivity for o-cresol based on phenol (B): 48.7%
A+B: 98.8%

The attrition resistance of the catalyst determined before use in the reaction was 1.8%; and the attrition resistance of the catalyst determined after use in the reaction (24 hours after the beginning of the reaction) was 2.1%.

EXAMPLE 18

Substantially the same procedures as in Example 1 were repeated to prepare a catalyst comprising a metal oxide containing as the metal component Fe and V in an atomic ratio of 1:1 and supported on 50% by weight, based on the catalyst, of silica, except that the catalyst was pre-calcined at 350° C. for 2 hours, followed by calcination at 800° C. for 3 hours. 500 g of the thus obtained catalyst was added to 81.0 g of a 2.5% by weight aqueous solution of potassium carbonate. While thoroughly stirring, the resulting mixture was dried at 100° C., followed by calcination at 700° C. for 2 hours. Thus, a catalyst comprising a metal oxide containing as the metal component Fe, V and K in an atomic ratio of 1:1:0.01 and supported on 50% by weight, based on the catalyst, of silica.

Using 300 g of the above-prepared catalyst, a continuous operation for the methylation of phenol with methanol was carried out in substantially the same manner as in Example 1. The reaction temperature and linear velocity were 335° C. and 7.2 cm/sec, respectively. The conversion of phenol and selectivities for 2,6-xylenol and o-cresol each based on phenol were determined at the end of a 24-hour operation period. The results were as follows.
Conversion of phenol: 87.2%
Selectivity for 2,6-xylenol (A): 53.0%
Selectivity for o-cresol (B): 45.7%
A+B: 98.7%

The attrition resistance of the catalyst determined before use in the reaction was 0.9%; and the attrition resistance determined after use in the reaction (24 hours after the beginning of the reaction) was 0.9%.

COMPARATIVE EXAMPLES 10 TO 14

Substantially the same procedures as in Example 1 were repeated to react phenol with methanol, except that a fixed bed reactor comprising a 2 cm-inner diameter glass tube packed with 6 cc of the same catalyst as used in Example 1 was used. The conversion of phenol, selectivity for the ortho-methylated phenol derivatives based on phenol and selectivity for the ortho-methylated phenol derivatives based on methanol was determined at the end of a 24-hour operation period. The results are shown in Table 4 below, in comparison with the results of Example 1.

According to substantially the same procedures as described above, the reactions of phenol with methanol were carried out, except that the same catalysts as used in Example 8, 12, 13 and 14 were respectively used. The results are shown in Table 4 below, in comparison with the results of Examples 8, 12, 13 and 14.

It is seen from Table 4 that the methylation of the ortho position of phenol with methanol by the fixed bed process is extremely poor in selectivity for the ortho-methylated phenol derivatives based on methanol as compared with that by the fluidized bed process of the present invention.

TABLE 4

| Example No. | Catalyst | | | | Reaction conditions | | | Results | | |
|---|---|---|---|---|---|---|---|---|---|---|
| | Metal Oxide Metal component and atomic ratio | Silica (% by weight) | Calcination temp. (°C.) | Type of bed | Molar ratio of raw materials (Phenol:methanol:water) | Reaction temp. (°C.) | Reaction time (hr) | Conversion of phenol (%) | Selectivity for ortho-methylated product (%)* | |
| | | | | | | | | | based on phenol | based on methanol |
| Example 1 | V:Fe = 1:1 | 50 | 750 | fluidized bed | 1:5:3 | 320 | 24 | 83.0 | 97.4 | 80.0 |
| Comparative Example 10 | " | 50 | 750 | fixed bed | " | 320 | 24 | 86.4 | 97.2 | 61.3 |
| Example 8 | V:Fe:K = 1:1:0.025 | 50 | 680 | fluidized bed | 1:7:3 | 330 | 24 | 86.3 | 98.5 | 78.5 |
| Comparative Example 11 | " | 50 | 680 | fixed bed | " | 330 | 24 | 87.6 | 98.4 | 60.0 |
| Example 12 | Fe:Cr = 1:0.1 | 50 | 500 | fluidized bed | 1:8:0 | 350 | 24 | 90.7 | 97.1 | 75.1 |
| Comparative Example 12 | " | 50 | 500 | fixed bed | " | 350 | 24 | 91.5 | 97.0 | 64.8 |
| Example 13 | Mn | 30 | 750 | fluidized bed | " | 400 | 24 | 90.5 | 97.3 | 70.8 |
| Comparative Example 13 | " | 30 | 750 | fixed bed | " | 400 | 24 | 89.1 | 97.3 | 59.1 |
| Example 14 | Mg | 50 | 600 | fluidized bed | 1:5:3 | 550 | 24 | 95.0 | 97.0 | 71.6 |
| Comparative Example 14 | " | 50 | 600 | fixed bed | " | 550 | 24 | 94.8 | 96.8 | 53.8 |

Note:
*Selectivity for ortho-methylated product is a total value of the selectivity for 2,6-xylenol and selectivity for o-cresol

EXAMPLE 19

To a solution of 585 g of ammonium metavanadate ($NH_4VO_3$) in 12,400 g of pure water heated at 90° C. were added, while vigorously stirring the solution, 2,020 g of ferric nitrate [$Fe(NO_3)_3.9H_2O$], 12.8 g of potassium nitrate ($KNO_3$), 3.5 g of lithium nitrate ($LiNO_3$) and 2,950 g of SNOWTEX-N (trademark of a silica sol manufactured and sold by Nissan Kagaku Kabushiki Kaisha, Japan) containing 30% by weight of $SiO_2$, whereby the raw material slurry was obtained. The raw material slurry was spray-dried in the same manner as in Example 1. The resulting dry powder was transferred to a tunnel type calcining kiln and pre-calcined at 350° C. for 2 hours, followed by calcination at 700° C. for 3 hours. Thus, there was obtained a catalyst comprising a metal oxide containing as the metal component V, Fe, Cr, Li and K in an atomic ratio of 1:1:0.06:0.01:0.025 and supported on 50% by weight, based on the catalyst, of silica. The surface area of the obtained catalyst was 4.0 m²/g as determined according to the BET method using nitrogen gas. It was confirmed by means of an electron microscope that the catalyst particles had a spherical shape suitable for use in the fluidized bed process. The average particle diameter and particle size distribution of the catalyst particles were determined by the microscopic method.

Average particle diameter: 48μ

Particle size distribution:
  0.2 to 0.7 time the average particle diameter; 38% by weight;
  1.5 to 2.0 times the average particle diameter; 15% by weight;
  More than 2.0 times the average particle diameter; 1.1% by weight.

300 g of the above-prepared catalyst was put into a 1.5 inch-diameter fluidized bed reactor. A mixture of phenol, methanol and water in a molar ratio of 1:5:3 was fed to an evaporator. The resulting gas was passed through the reactor at a linear velocity of 3.3 cm/sec (contact time: 8 sec) to effect a continuous operation for the methylation of phenol with methanol while maintaining the reaction temperature at 325° C. and the reaction pressure at zero (atmospheric pressure). The conversion of phenol, selectivity for the ortho-methylated phenol derivatives based on phenol and selectivity for the ortho-methylated phenol derivatives based on methanol were determined at the respective ends of the operation periods as indicated in table 5 below. The results are shown in Table 5 below.

The attrition resistance of the catalyst determined before use in the reaction was 1.2%; and the attrition resistance of the catalyst determined after use in the reaction (600 hours after the beginning of the reaction) was 1.1%.

COMPARATIVE EXAMPLE 15

To a solution of 292.5 g of ammonium metavanadate ($NH_4VO_3$) in 6,200 g of pure water heated at 90° C. were added, while vigorously stirring the solution, 1,010 g of ferric nitrate [$Fe(NO_3)_3.9H_2O$], 60 g of chromic nitrate [$Cr(NO_3)_3.9H_2O$], 6.4 g of potassium nitrate ($KNO_3$) and 1.75 g of lithium nitrate ($LiNO_3$), whereby the raw material slurry was obtained. The above-obtained slurry was evaporated to dryness on a hot water bath, followed by pre-calcination at 350° C. for 2 hours. To 300 g of the pre-calcined catalyst was added 1,000 g of SNOWTEX-N (trademark of a silica sol manufactured and sold by Nissan Kagaku Kabushiki Kaisha, Japan) containing 30% by weight of $SiO_2$. While stirring, the resulting slurry was subjected to evaporation on a hot water to an extent that the catalyst can be molded. The catalyst was molded into cylindrically shaped pellets having a diameter of 5 mm and a length of 5 mm. The catalyst was dried at 100° C. for 12 hours and then calcined at 700° C. for 3 hours. Thus, a catalyst for use in a fixed bed process having the same composition that as in Example 19 was obtained.

150 cc of the above-prepared catalyst was packed in a one-inch inner diameter fixed bed reactor. A mixture of phenol, methanol and water in a molar ratio of 1:5:3 was fed to an evaporator. The resulting gas was passed through the reactor at a linear velocity of 3.7 cm/sec (contact time: 8 sec) to effect a continuous operation for the methylation of phenol with methanol while maintaining the reaction pressure at zero kg/cm²-G (atmospheric pressure). The reaction at 325° C. was tried. But, the temperature of the fixed bed was different from portion to portion and the difference between the maximum temperature and the minimum temperature in the fixed bed was about 15° C. Therefore, the reaction was carried out while maintaining the maximum temperature in the fixed bed at 325° C. The conversion of phenol, selectivity for the ortho-methylated phenol derivatives based on phenol and selectivity for the ortho-methylated phenol derivatives based on methanol were determined at the respective ends of operation periods as indicated in Table 5 below. The results are shown in Table 5 below.

As is seen from Table 5, the selectivity for the ortho-methylated derivatives based on methanol is very low in the fixed bed process as compared with that in the fluidized bed process, and is drastically decreased with the lapse of reaction operation time.

from the group consisting of hydrogen, methyl, ethyl, isopropyl and tertiary butyl, through a fluidized bed, operated at a temperature of 250° to 600° C., of particles of a catalyst comprising 30 to 70% by weight of silica and 70 to 30% by weight of a metal oxide having a catalytic activity in the methylation of the ortho position of a phenol and supported on said silica, said metal oxide containing as the metal component at least one metal selected from the group consisting of iron, vanadium, manganese, magnesium, chromium and indium, said catalyst having been calcined at 500° to 900° C.

2. A process according to claim 1, wherein said catalyst has an average particle diameter of 30 to 120μ, and

TABLE 5

| | Catalyst | | | | Reaction conditions | | | Results | | | |
|---|---|---|---|---|---|---|---|---|---|---|---|
| | Metal oxide Metal | | Calci- | | Molar ratio of raw materials | Reac- | Reac- | Conver- | Selectivity for ortho-methylated product (%)* | | |
| Example No. | component and atomic ratio | Silica (% by weight) | nation temp. (°C.) | Type of bed | (Phenol: methanol: water) | tion time (hr) | tion temp. (°C.) | sion of phenol (%) | based on phenol | based on methanol | Remarks |
| Example 19 | V:Fe:Cr:Li:K = | 50 | 700 | fluid- | 1:5:3 | 24 | 325 | 90.5 | 98.5 | 78.4 | There was no |
| | 1:1:0.06: | | | ized | | 120 | 325 | 91.2 | 99.2 | 78.5 | temperature |
| | 0.01:0.025 | | | bed | | 240 | 325 | 90.4 | 99.0 | 77.9 | difference |
| | | | | | | 600 | 327 | 91.5 | 99.1 | 78.3 | from portion to portion in the fluidized bed. |
| Comparative Example 15 | V:Fe:Cr:Li:K = | " | " | fixed | " | 24 | 325 | 91.1 | 98.3 | 72.1 | The difference |
| | 1:1:0.06: | | | bed | | 120 | 327 | 91.0 | 98.6 | 70.6 | between the |
| | 0.01:0.025 | | | | | 240 | 330 | 90.6 | 98.3 | 67.4 | maximum temperature and minimum temperature in the fixed bed was about 15° C. |
| | | | | | | 600 | 335 | 90.9 | 97.5 | 59.7 | |

Note:
*Selectivity for ortho-methylated product is a total value of the selectivity for 2,6-xylenol and selectivity for o-cresol.

What is claimed is:

1. A process for methylating a phenol at the ortho position which comprises flowing a gaseous stream containing methanol and a phenol having the general formula

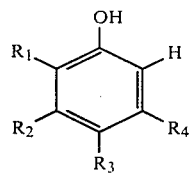

wherein $R_1$, $R_2$, $R_3$ and $R_4$ each independently represent a saturated aliphatic hydrocarbon substituent selected has a particle size distribution such that the catalyst comprises (A) catalyst particles having particle diameters of 0.2 to 0.7 time said average particle diameter, (B) catalyst particles having particle diamters of 1.5 to 2.0 times said average particle diameter and (c) catalyst particles having particle diameters of more than 2.0 times said average particle diameter, the proportions of (A), (B) and (C) in the catalyst being 5 to 50%, 5 to 30% and 0 to 10% by weight, respectively.

3. A process according to claim 1, wherein said metal oxide further contains as an auxiliary metal component at least one metal selected from the group consisting of alkaline metals, alkaline earth metals and rare earth metals.

* * * * *

UNITED STATES PATENT AND TRADEMARK OFFICE
CERTIFICATE OF CORRECTION

PATENT NO. : 4,517,389                     Page 1 of 2
DATED      : May 14, 1985
INVENTOR(S): Tsutomu Katsumata, et al.

It is certified that error appears in the above-identified patent and that said Letters Patent is hereby corrected as shown below:

| | |
|---|---|
| 1st page, under "U.S. Patent Documents" | Line 12, delete "5/1982" and substitute --11/1982-- |
| Col. 4, line 11 | Correct spelling of "saturated" |
| Col. 4, line 49 | Before "ortho-" insert --the-- |
| Col. 5, line 43 | Correct spelling of "chromium" |
| Col. 7, line 48 | Correct spelling of "magnesium" |
| Col. 12, Table 1, line 8 under last column heading | Delete " " " and substitute --1:7:3-- |
| Col. 11, Table 1 | Delete Example 1 across the Table and substitute: |

--Example 1   4.6   24    320   83.0   44.1   53.3
                    120   322   82.8   43.5   54.2
                    240   325   82.7   43.0   54.9

97.4   0.02          0.80   1.35  --
                          97.7   0.02
                          97.9   0.02

UNITED STATES PATENT AND TRADEMARK OFFICE
CERTIFICATE OF CORRECTION

PATENT NO. : 4,517,389
DATED : May 14, 1985
INVENTOR(S) : Tsutomu Katsumata, et al It is certified that error appears in the above-identified patent and that said Letters Patent is hereby corrected as shown below:

Col. 15, line 20    Delete "as" and substitute --was--

Signed and Sealed this

Fifth Day of November 1985

[SEAL]

Attest:

Attesting Officer

DONALD J. QUIGG

Commissioner of Patents and Trademarks